United States Patent [19]
Anderson

[11] Patent Number: 5,422,718
[45] Date of Patent: Jun. 6, 1995

[54] ELASTIC-PART IMMERSION CELL FOR ANALYZING MICROSTRUCTURES IN MATERIALS

[75] Inventor: Alan J. Anderson, Blacksburg, Va.

[73] Assignees: The Center for Innovative Technology, Herndon; Virginia Polytechnic Institute & State University; Virginia Tech Intellectual Properties, Inc., both of Blacksburg, all of Va.

[21] Appl. No.: 59,906

[22] Filed: May 10, 1993

[51] Int. Cl.$^6$ ............................................. G01N 21/01
[52] U.S. Cl. ..................... 356/244; 356/30; 356/31
[58] Field of Search ................ 356/30, 31, 244, 246, 356/138, 361, 363, 153, 128, 440; 359/391, 394, 398, 385, 798, 804; 378/73, 75, 78, 81; 250/576, 226

[56] References Cited

U.S. PATENT DOCUMENTS

| | | | |
|---|---|---|---|
| 2,352,072 | 6/1944 | Bond | 356/31 |
| 2,381,993 | 8/1945 | Baker | 356/31 |
| 2,387,825 | 10/1945 | Bond | 356/31 |
| 3,614,229 | 10/1971 | Denne | 356/31 |
| 4,152,069 | 5/1979 | Bruck | 356/30 |
| 4,906,083 | 3/1990 | Sattler | 356/30 |

OTHER PUBLICATIONS

De Hoff, "Quantitative serial sectioning analysis: preview," J. of Microscopy, 131:259–263 (12/1982).
Petford et al., "Three–dimensional imaging of fission tracks using confocal scanning laser microscopy," Am. Mineralogist, 77:529–533 (1992).
Bloss, "The spindle stage: a turning point for optical crystallography," Am. Mineralogist, 63:433–447 (1973).
Roy, "A modified spindle stage permitting the direct measurement of 2V," Am. Mineralogist, 50:1441–1449 (1965).
Jones, "Spindle stage with easily changed liquid and improved crystal holder," Am. Mineralogist, 53:1399–1403 (7/1968).
Grattan–Bellew, "A modified spindle for the detent spindle stage," Am. J. of Science, 274:829–830 (1974).

Primary Examiner—Hoa Q. Pham
Attorney, Agent, or Firm—Whitham, Curtis, Whitham & McGinn

[57] ABSTRACT

The elastic-port immersion cell (10) is an optical oil immersion vessel which has a flexible latex (or other) sheath (24) protruding from its sidewall. The sheath is affixed to an opening in the wall of the vessel using a collar, O-ring (26) or other connecting means. The base of the vessel is an optical glass window. A sample (20) mounted on to the end of spindle (14) is placed into the cell. The end of the spindle (14), without the sample, is inserted into the sheath and the latex together with the spindle is attached to a goniometer head of a spindle stage such that the spindle is horizontal. Immersion oil (22) that has a refractive index similar to the sample is added to the cell until the sample is totally submerged. Minute features within the sample (20) may then be observed under the microscope as the sample is rotated 360 degrees about a vertical or horizontal axis. The latex sheath prevents the oil from escaping from the cell and also provides the flexibility required to orient and rotate a sample.

8 Claims, 5 Drawing Sheets

ELASTIC-PART IMMERSION CELL FOR ANALYZING MICROSTRUCTURES IN MATERIALS

BACKGROUND OF THE INVENTION

1. Field of the Invention

This invention is generally related to instrumentation used for analyzing microstructures in minerals. More particularly, the invention allows an inexpensive and effective means for observing fluid inclusions, microcracks, and other structures within crystal and other mineral samples.

2. Description of the Prior Art

Morphometric analysis of objects or structures within translucent materials is of considerable interest to geologists and materials scientists. The orientation of planar and linear arrays of fluid inclusions with respect to crystallographic directions in the host mineral is the most important characteristic for determining the temporal classification of inclusions. Knowledge of the orientation of inclusion planes relative to macrostructural features in the host rock is necessary to understand the timing of various fluid events with respect to the tectonic and deformational history of the rock. In addition, the size and shape of individual fluid inclusions and their contained phases must be known for many important applications.

At the present time, there is no inexpensive, straightforward method for analyzing microstructures such as fluid inclusions and microcracks within mineral samples.

In standard petrographic techniques, the sample is observed in only two dimensions. Three-dimensional properties can be inferred from the two dimensional images using sophisticated mathematical models. De Hoff, *J. of Microscopy*, 131:259-263 (1982), disclose a technique for quantitative serial sectioning analysis for characterizing three-dimensional microstructures from two-dimensional image information.

Recently, Petford et al., *Am. Mineralogist*, 77:529-533 (1992) disclosed three-dimensional imaging of fluid inclusions using confocal scanning laser microscopy. In operation, confocal three-dimensional images are achieved by compiling serial sections through the sample with the aid of image analysis software. Despite the advantages, this technique has the disadvantages of requiring a very high instrumentation cost, requiring very complex equipment and software which is not easily understood by researchers, and requiring correction for the refractive index of the host material. Furthermore, materials that are transparent to white light may not be easily observed with laser light.

The spindle stage is a simple and powerful tool used to measure the optical constants of anisotropic crystals by immersion techniques. The attributes and functions of the spindle stage are discussed in detail in Bloss, *Am. Mineralogist*, 63:433-447 (1973) and Bloss, *The Spindle Stage: Principles and Practice*, Cambridge University Press, New York, 1981, 340 pages. For optical studies, it is expedient to use crystals that are typically less than one millimeter (1 mm) in diameter. Therefore, conventional spindle stages are equipped with a shallow immersion cell that is sufficient to completely bathe a tiny crystal in oil. Modified spindle stages are described in Roy, *Am. Mineralogist*, 50:1441-1449 (1965), Jones, *Am. Mineralogist*, 53:1399-1403 (1968), and Grattan-Bellew, *Am. K. of Science*, 274:829-830 (1974). Each of these modified spindle stages are utilized for analyzing very small crystal samples, and each includes the use of an immersion cell with an open side. Oil is retained in the immersion cell via the surface tension with the top and bottom plates, and by adding blotting paper between the plates. Since only small crystal samples are used, oil leakage from the immersion cell is minimal.

Prior to this invention, the spindle stage had not been used for analyzing structures such as fluid inclusions and microcracks in larger mineral samples.

SUMMARY OF THE INVENTION

It is an object of this invention to provide a device suitable for observing microcracks, fluid inclusions, and other structures, in larger (e.g., greater than 2 mm in diameter) mineral samples using a spindle stage.

According to the invention, a spindle holding large sized mineral samples on the order of 0.5 cm or more in diameter projects into a spindle vessel which contains enough oil to submerge the mineral sample. The spindle projects through a side opening in the spindle vessel, and a film, preferably made of latex, is connected to prevent escape of oil from the spindle vessel and separates the oil from the goniometer head. The film provides the flexibility required to orient a given inclusion body or microcrack for examination purposes by translation or rotation of the spindle with the goniometer head "and is flexible enough to allow 360° rotation of the spindle through said side port without tearing or excessive torque".

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1A:
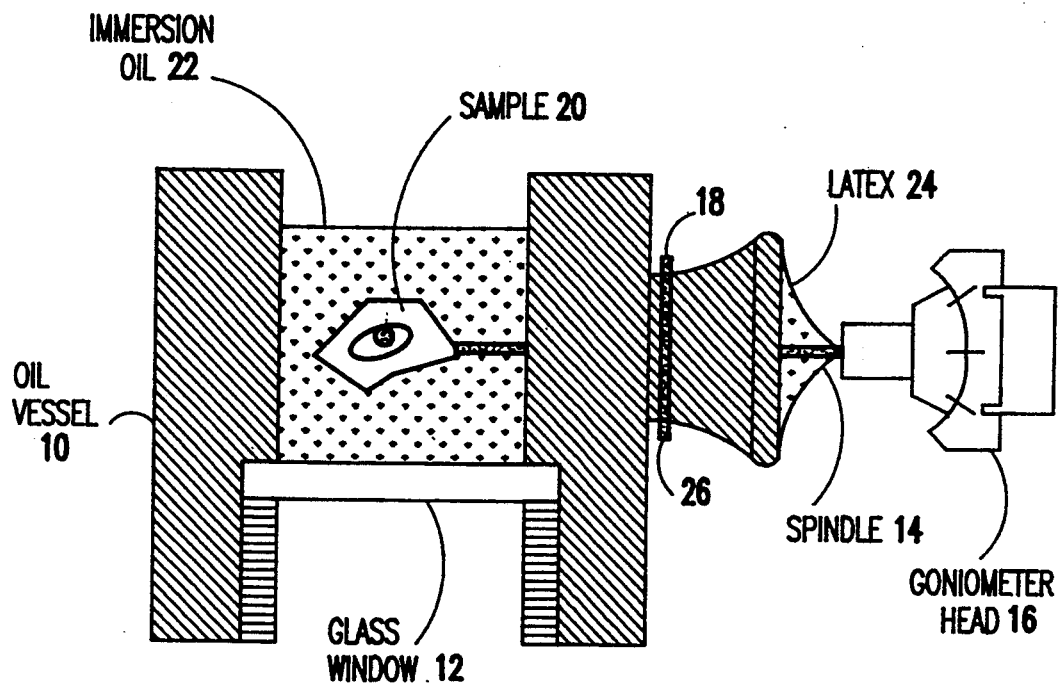
FIGS. 1a and 1b are schematic diagrams of the spindle vessel according to this invention.
Figure 1B:
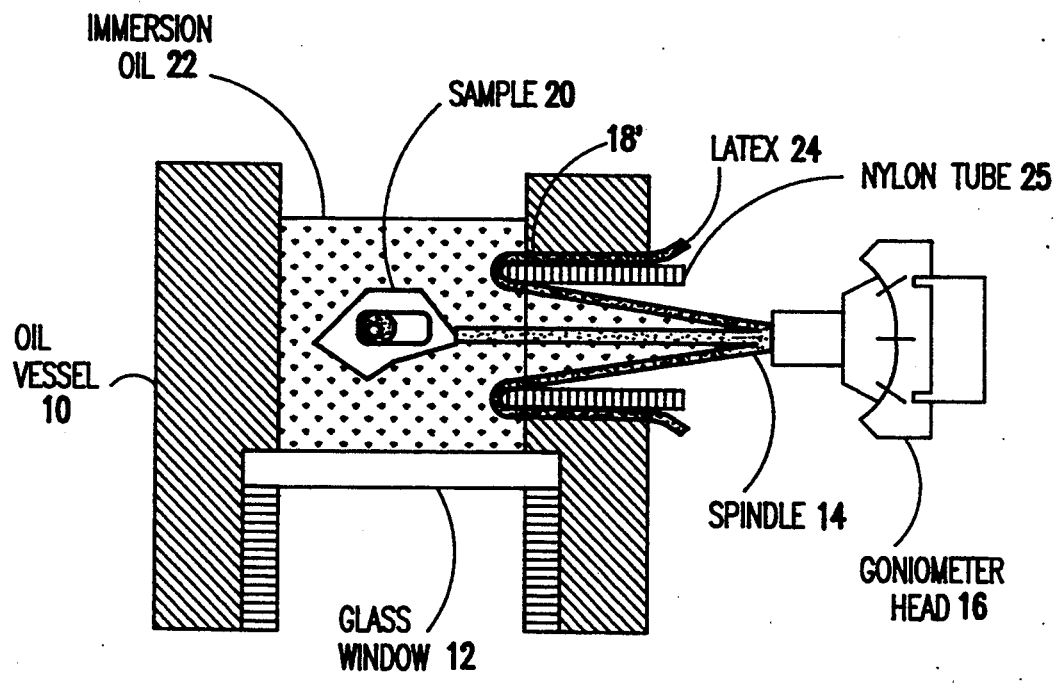

FIGS. 1a and 1b are schematic drawings of the modified spindle stage of the present invention where there is shown an oil immersion vessel 10 which can be machined out of aluminum, polytetrafluoroethylene, or any other suitable material. An optical glass window 12 of which diameter is in the range of lesser or greater than 2.0 cm serves as the bottom of the vessel 10. The spindle 14 extends from the goniometer head 16 into the oil immersion vessel 10 through side opening 18 or 18'. The spindle 14 is generally longer than the brass pins used for single crystal X-ray diffraction studies and can be on the order of 24 mm or more in length. The spindle 14 can be made of aluminum, glass fiber, or other suitable materials. A mineral sample 20, which can be crystal in nature and can have a diameter on the order of 0.5 cm or more (although small sized crystals of 2 mm or less can also be used) is glued to the end of the spindle 18 using cyanoacrylic cement of the like. The oil immersion vessel 10 is filled with oil 22 which covers the mineral sample 20. The oil immersion vessel 10 is preferably greater than 1 cm in diameter and 1 cm in depth; however, the size of the samples 20 can dictate smaller and larger volumes for the oil immersion vessel 10.

FIG. 1a shows an elastic film 24, preferably made of latex, is connected to the side opening 18 of the oil immersion vessel 10 using an O-ring 26 or other suitable connector. FIG. 1b shows the elastic film 24 is connected to the side opening 18' by wrapping the film 24 around a nylon collar 25 and inserting the collar in the opening 18'. The latex film 24 separates the spindle 14 from the goniometer head 16 and prevents the immersion oil 22 from leaking out of the vessel 10. Experience has shown that less leakage occurs with the nylon collar 25 arrangement of FIG. 1b. Furthermore, the latex film 24 provides the flexibility required to orient microcracks and fluid inclusions within the sample 20 using the goniometer head 16. Standard immersion oil will dissolve latex, therefore it is necessary to use a refractive index oil that is compatible with latex such as Laser Liquid which is sold by the Cargille company, or the like.

The oil immersion vessel 10 can be sized to accommodate samples as large as 1–5 cm in diameter, but in practice the maximum sample size depends on the clarity of the sample. Spindles intended to hold doubly polished plates have a slot cut into one end where the plate is to be inserted. For the analysis of microcracks, oriented samples are sectioned and cut into rectangular prisms where the long dimension of the prism is cut parallel to a reference azimuth. The upper surface of the prisms should be identified with a dot or other suitable marking. The size of the rectangular prisms can vary; however, good results can be obtained with prisms that are 7×2×1 mm which are mounted on an aluminum spindle.

In operation, once the sample 20 is securely mounted, the opposite end of the spindle 14 is pressed into the latex film 24 and inserted into the goniometer head. The sample 20 is then positioned into the oil vessel 10 through the side opening 18 or 18'. The latex film 24, which envelops the spindle 14, is either sealed around the opening 18 using an O-ring or sealed into the opening 18' using a collar or other tubular element. Immersion oil 22 which has a refractive index that matches a principal index of the host mineral is added to the vessel 10 with a piper or by other means until the mineral sample 20 is totally immersed. The level of immersion oil 22 in the vessel 10 must be well above the spindle 14 so that the mounted sample 20 remains totally submerged throughout its rotation. A circular glass cover slide (not shown) can be placed on top of the vessel 10 to contain the fumes from the immersion oil 22. Microscope objectives with a long working distance must be used to view the sample within the oil vessel 10, and a long working-length substage condenser is also recommended for optimum optics.

With the spindle stage, a crystal can be rotated 360° about either a vertical (microscope stage) or horizontal (spindle) axis, so that any desired linear feature in the crystal may be rotated into the plane of the microscope stage, thus allowing all three principal indices to be directly determined from the same grain. Similarly, any planar feature can be rotated about a horizontal axis until it is in the vertical plane, allowing the orientation of the feature with respect to some other feature (crystallographic axis) or external feature to be determined.

In operation, the orientation of planar or linear features are measured with respect to a reference direction. The degrees of rotation is measured from the graduations on the microscope stage and the spindle drum. The reference direction may be: an optical constant derived from extinction measurements, a crystallographic feature such as a cleavage plane, growth zone, crystal face (positive or negative), or a twin plane; a microstructural or macrostructural feature in the host mineral; or an azimuth and horizontal surface marked on an oriented sample taken from the field. Determination of optical directions in a crystal can be facilitated using computer programs such as EXCALBR II. If a quartz crystal exhibits strained extinction an alternative method may be necessary to determine its crystallographic orientation.

Figure 2A:
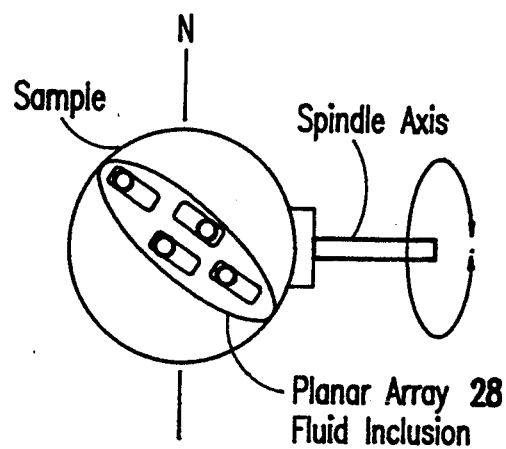
FIGS. 2a-c are sequential schematic views of a magnified planar feature in a sample being oriented for analysis.
Figure 2B:
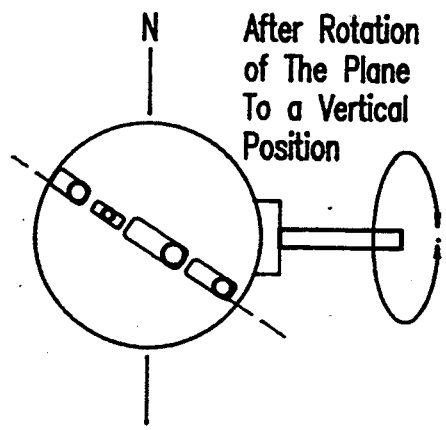
Figure 2C:
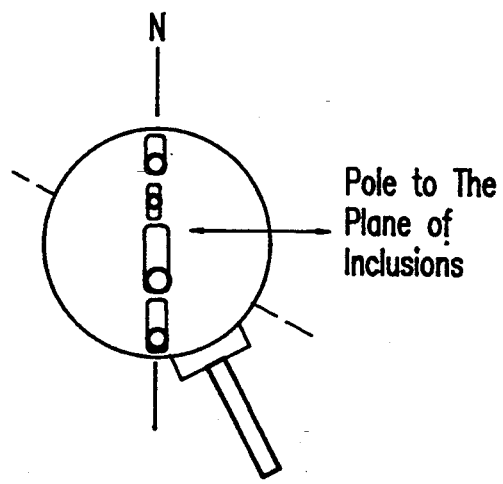

FIGS. 2a–c illustrate the procedure used to determine the pole to a planar feature. First, a planar array of inclusions 28, dipping at some unknown angle to the mounted sample, is selected. The plane is rotated about the horizontal axis until it is vertical. The vertical orientation of a planar feature may be checked, as shown in FIG. 2b, by focussing through the sample to see if the position of the plane shifts in a lateral sense. Finally, the plane is rotated about the axis of the microscope stage until it is oriented to the north-south cross hair of the eyepiece. The pole of the plane, which is now horizontal and east-west, can be measured relative to a starting reference position, by the amount of rotation about the horizontal and vertical axes as indicated in the graduations around the edge of spindle drum and microscope stage, respectively.

To determine a lineation direction, a linear feature within the crystal is rotated about the horizontal axis into the plane of the microscope stage. It is then rotated about the vertical axis to an east-west direction. The amount of rotation about each axis with respect to a reference position is then recorded and plotted on a stereonet.

Figure 3A:
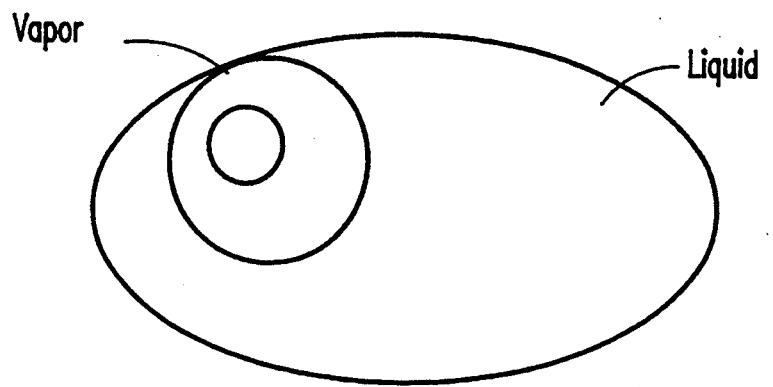
FIGS. 3a-b are mutually perpendicular views of a fluid inclusion used for determining the dimensions and volume of the fluid inclusion.
Figure 3B:

The modified spindle stage may also be used to measure the size and shape of an individual fluid inclusion and its contained phases. By rotating a fluid inclusion about the spindle axis, its dimensions can be measured from observation in two mutually perpendicular directions. FIGS. 3a–b show a fluid inclusion observed from orthogonal directions. These dimensions can be measured using a graduated ocular or a calibrated image analysis system.

Figure 4:
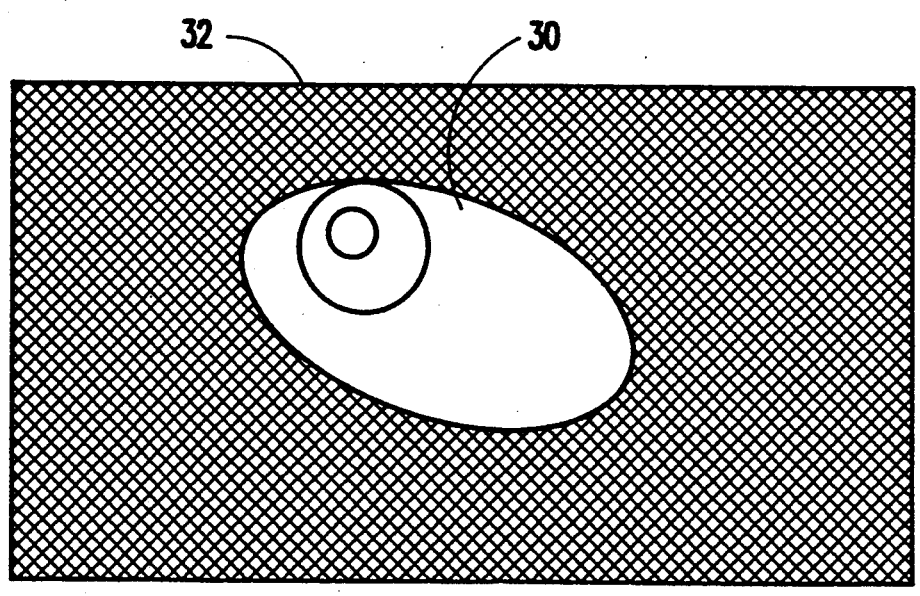
FIG. 4 is a view of a subsurface fluid inclusion showing the distance beneath the surface at which the fluid inclusion is located.

The distance between a given inclusion and some other inclusion or feature in the sample may also be easily determined with the modified spindle stage. For example, FIG. 4 shows the depth of an inclusion 30 below the surface 32 of a host mineral can be directly measured once the polished surface of the mineral plate has been rotated into a vertical position. By viewing the sample parallel to the polished surface, one can readily locate shallow fluid inclusions that are suitable for in situ microanalysis. For these measurements, it is useful to cross the nicols of the microscope in order to clearly define the interface between the mineral and an immersion oil of matching refractive index.

The ability to determine the geometric features of fluid inclusion planes or individual inclusions has application to many important inclusion-related problems. However, it should be understood that the three-dimensional observation afforded by the modified spindle stage of this invention is not limited to fluid inclusion studies, but is also ideally suited to other studies involving microscopic observation in which the orientation of the feature being observed is important. These studies include, among others, microstructural analysis of deformed materials and fission track measurements. The following examples illustrate the utility of the modified spindle stage for particular applications.

EXAMPLE 1

The modified spindle stage can be used to identify primary fluid inclusions. The assignment of inclusion origin is the single most critical stage in the study of natural fluid inclusions. The empirical criteria used to identify inclusions of primary and secondary origin are based to a large extent on the distribution and orientation of inclusions with respect to crystallographic directions of the host mineral, and on the size and shape of the inclusions. Relating an inclusion or group of inclusions to a crystallographic direction in the host mineral is difficult, particularly when the host mineral does not display visible zoning. With this invention, the angular relations between a crystallographic direction in the host crystal and arrays of fluid inclusions can be precisely and easily determined. If the planes of fluid inclusions are not consistently parallel to prominent crystal directions, then it can be assumed that they are not primary fluid inclusions. The reverse, however, is not true. That is, fluid inclusions that occur along crystal growth directions are not always primary.

Figure 5A:
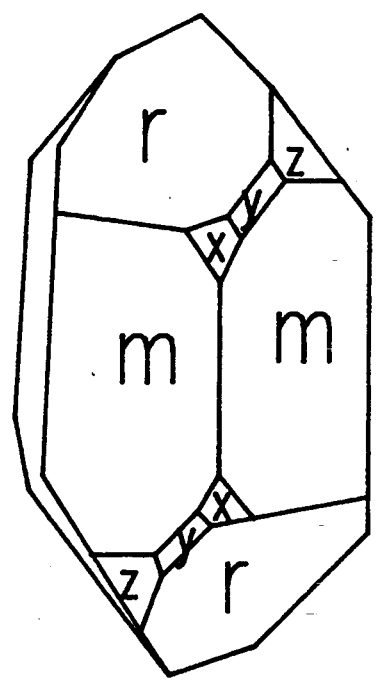
FIGS. 5a-b are isometric views showing crystallographic faces.
Figure 5B:
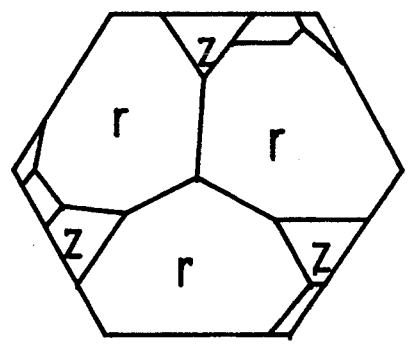

The most convincing evidence that a given group of fluid inclusions is primary is if the inclusions are restricted to a growth face in the host mineral. In the case of a mineral such as quartz that usually does not exhibit visible zoning, the angular relationship between optical constants and a planar array of fluid inclusions may be used to determine whether or not the inclusions were trapped on a growth surface. Although low quartz displays numerous crystal forms, trapping is most likely to occur on one or more of the five dominant form faces illustrated in FIGS. 5a and 5b. Thus, if the inclusions can be consistently related to one of these growth surfaces, one can claim with confidence that the inclusions are primary. Planes of secondary inclusions in quartz can occur along cleavages that are parallel to the rhombic faces, but these can usually be distinguished by their undulatory form (see, Roedder, *Min. Soc. of Am.*, 12:644 (1984)). With the modified spindle vessel of this invention, it is possible to determine not only if the inclusions occur along a growth surface, but also to determine the crystal face on which trapping occurred.

EXAMPLE 2

The modified spindle stage can be used to determine fluid inclusion phase ratios. Constant phase ratios in fluid inclusions is commonly cited as evidence for entrapment of homogenous fluid within a narrow range of temperature and pressure. Moreover, consistent phase ratios and microthermometric behavior amongst a group of inclusions is strong evidence that the inclusions have not leaked or re-equilibrated following entrapment. Conversely, the presence of coexisting vapor and Liquid rich fluid inclusions or inclusions with a range in liquid-to-vapor ratios provides evidence for immiscibility at the time of trapping or later leakage or necking. Visual estimates of fluid inclusion ratios from observation in two dimensions are unreliable and other researchers have recommended that two-dimensional evidence be confirmed by microthermometric analysis. However, as discussed above in conjunction with FIGS. 3a and 3b, evidence of coexisting liquid and vapor rich inclusions may be obtained using estimates of fluid inclusion phase ratios from observations in two mutually perpendicular directions of the fluid inclusion and the individual phases.

EXAMPLE 3

The modified spindle stage can be used for paleofracture analysis. Numerous studies have shown that the orientation of fluid healed fractures is a valuable paleostress indicator. Moreover, the angular relationship between planar arrays of secondary inclusions and microstructural and macrostructural features in the host rock can be used to correlate inclusion-decorated microcracks to specific deformational or mineralization events. For example, studying fluid inclusion with proven association with gold deposition may be an important research direction for improving the understanding of the nature and timing of mineralizing solutions in greenstone gold deposits.

Knowledge of the morphology, orientation, and density of annealed cracks in minerals is important to understanding paleo-permeability of a rock and how it evolved with time. For example, fluid inclusion orientation analysis is useful for reconstructing the geometry of fluid migration. Furthermore, precise measurements of the morphology of inclusions within annealed cracks will be useful for estimating inclusion formation conditions.

EXAMPLE 4

The modified spindle stage can be used for quantitative microanalysis of individual fluid inclusions. In situ analysis of single fluid inclusion by proton-induced x-ray emission (PIXE) or synchrotron X-ray fluorescence (SXRF) requires accurate measurement of the size of the fluid inclusion and its depth beneath the polished surface. Estimates of these parameters from observation in two dimensions can result in significant error in the calculated x-ray yields. Prior to this invention, the approximate depth of the inclusion was determined with a petrographic microscope by the vertical displacement of the objective lens from the focussed image of the polished surface to that of the fluid inclusion. The minimum and maximum depths of the inclusion extremities, however, cannot be reliably determined using this technique. However, as discussed above in conjunction with FIGS. 3a-b and FIG. 4, the size and volume of a fluid inclusion and its position below the host mineral surface can be easily and quickly determined using the modified spindle vessel of this invention. This invention provides reliable measurements for quantitative inclusion analysis because all three inclusion dimensions are reviewed.

EXAMPLE 5

The modified spindle stage can be used for the evaluation of decrepitation behavior. Numerous researchers have shown that the size and shape of inclusions are very important features controling decrepitation behavior of fluid inclusions. Thus, in order to predict when a given inclusion may have decrepitated naturally as a result of uplift or burial, the size and shape must be known. In the past, researchers have used the diameter of inclusions observed in two dimensions to approximate size; however, as discussed in conjunction with FIGS. 3a–b, the size and shape dimensions can be determined more accurately using the modified spindle stage of the present invention.

EXAMPLE 6

Figure 6A:
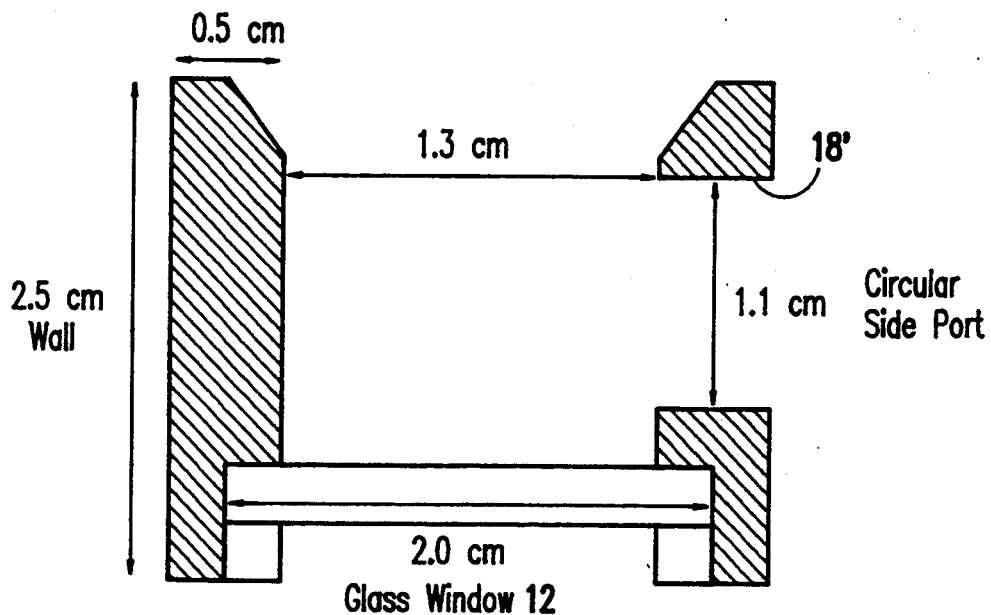
FIGS. 6a-c are plane views of the spindle vessel, nylon collar, and aluminum spindle showing dimensions of a working prototype spindle vessel according to the present invention.
Figure 6B:
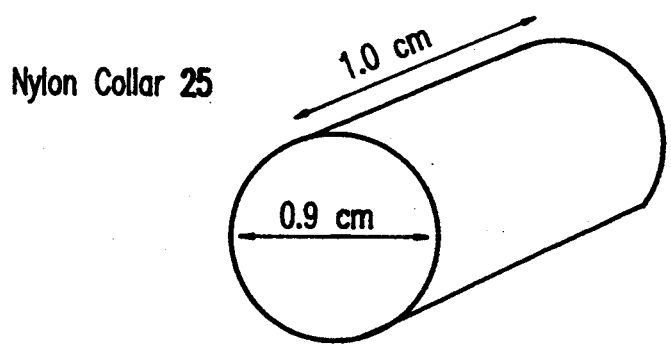
Figure 6C:
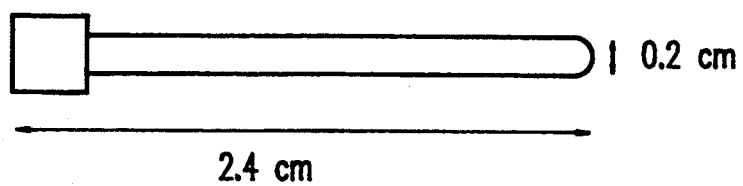

FIGS. 6a–c show the dimensions of a working prototype spindle vessel within the practice of this invention. FIG. 6a shows the oil vessel 10 has 2.5 cm high wall that is 0.5 cm thick, a 2.0 cm glass window 12 at its base, the walls separated by a distance of 1.3 cm, and a circular side port 18' of 1.1 cm. FIG. 6b shows that the nylon collar 25 is 0.9 cm in diameter and 1.0 cm long. FIG. 6c shows the aluminum spindle is 2.4 cm long and 0.2 cm wide.

The spindle vessel of this invention can also have other dimensions including, for example, sidewalls which have the height in the range of 0.5 to 1.0 cm, and a glass window of which diameter is in the range of lesser or greater than 2.0 cm.

While the invention has been described in terms of its preferred embodiments, those skilled in the art will recognize that the invention can be practiced with modification within the spirit and scope of the appended claims.

I claim:

1. A spindle vessel sized to fit on a stage of a microscope, comprising:
    a housing for containing a volume of immersion oil, said housing having upwardly projecting sidewalls a transparent bottom, said housing being rotatable about a vertical axis perpendicular to said stage of said microscope;
    a side port formed in a sidewall of said housing which allows a spindle to project into said volume of immersion oil within said housing from a goniometer head positioned outside said housing, said side port allowing said spindle to be rotated about a horizonal axis while said spindle is projected into said volume of immersion oil; and
    a means for preventing leakage of said volume of immersion oil from said housing through said side port,
    whereby a specimen connected to said spindle can be rotated about both said vertical axis and said horizontal axis for analysis of said specimen at different angular orientations with respect to said vertical axis and said horizontal axis.

2. The spindle vessel of claim 1 wherein said means for preventing is a film which is connected to said side port and to said spindle.

3. The spindle vessel of claim 2 wherein said film is connected to a base of said spindle which is insertable into a goniometer head.

4. The spindle vessel of claim 2 wherein said film is connected to an external surface of said side port.

5. The spindle vessel of claim 2 wherein said film is through a collar and folded over an outer surface of said collar, said collar being inserted in said side port and said film folded over said outer surface of said collar being fluid tight with said side port.

6. The spindle vessel of claim 2 wherein said film is flexible enough to allow 360° rotation of said spindle through said side port without tearing or excessive torque.

7. The spindle vessel of claim 1 wherein said upwardly projecting sidewalls are greater than 0.5 cm in height.

8. The spindle vessel of claim 1 wherein said diameter of said transparent bottom of said housing is 1 cm or greater.

* * * * *